United States Patent [19]

Allard et al.

[11] Patent Number: 5,434,051
[45] Date of Patent: Jul. 18, 1995

[54] ASSAY WITH SIGNAL DETECTION IN THE PRESENCE OF A SUSPENDED SOLID SUPPORT

[75] Inventors: William J. Allard; David M. Obzansky, both of Elkton, Md.; Hermant C. Vaidya, Wilmington, Del.

[73] Assignee: E. I. Du Pont de Nemours and Company, Wilmington, Del.

[21] Appl. No.: 89,060

[22] Filed: Jul. 8, 1993

Related U.S. Application Data

[63] Continuation of Ser. No. 736,543, Jul. 26, 1991, abandoned.

[51] Int. Cl.$^6$ .............................................. G01N 33/573
[52] U.S. Cl. .................................... 435/7.4; 435/7.91; 435/7.94; 435/966; 436/525; 436/530; 436/534; 436/805; 356/433; 356/441
[58] Field of Search ............ 435/7.4, 7.91, 7.94, 435/966, 968; 436/525, 526, 530, 531, 534, 817, 818, 805; 356/307, 320, 407, 433, 441

[56] References Cited

U.S. PATENT DOCUMENTS

| | | | |
|---|---|---|---|
| 3,852,157 | 12/1974 | Rubenstein et al. | 195/63 |
| 4,012,146 | 3/1977 | Fujita et al. | 356/320 X |
| 4,098,876 | 7/1978 | Piasio et al. | 424/1 |
| 4,115,535 | 9/1978 | Giaever | 436/818 X |
| 4,244,940 | 1/1981 | Jeong et al. | 424/1 |
| 4,259,232 | 3/1981 | Carrico et al. | 260/112 R |
| 4,318,982 | 3/1982 | Hornby et al. | 435/7 |
| 4,378,428 | 3/1983 | Farina et al. | 435/7 |
| 4,463,090 | 7/1984 | Harris | 435/7 |
| 4,486,530 | 12/1984 | David et al. | 435/7 |
| 4,555,484 | 11/1985 | LaRossa et al. | 435/21 |
| 4,598,042 | 7/1986 | Self | 435/7 |
| 4,656,143 | 4/1987 | Baker et al. | 436/527 |
| 4,661,408 | 4/1987 | Lau et al. | 428/405 |
| 4,693,969 | 9/1987 | Saxena et al. | 435/7 |
| 4,745,054 | 5/1988 | Rabin et al. | 435/6 |
| 4,757,016 | 7/1988 | Klenner et al. | 435/188 |
| 4,912,033 | 3/1990 | Ladenson et al. | 435/7 |
| 4,914,023 | 4/1990 | Philo | 435/7 |
| 4,954,435 | 9/1990 | Krauth | 436/518 X |
| 5,093,271 | 3/1992 | Yamamoto | 436/518 |

FOREIGN PATENT DOCUMENTS

| | | |
|---|---|---|
| 0123265 | 10/1984 | European Pat. Off. . |
| 0149565 | 7/1985 | European Pat. Off. ............ 436/526 |
| 173973 | 3/1986 | European Pat. Off. . |
| 0216177 | 4/1987 | European Pat. Off. . |
| 0270291 | 6/1988 | European Pat. Off. . |
| 0288179 | 10/1988 | European Pat. Off. . |
| 0296544 | 1/1989 | European Pat. Off. . |
| 0358948 | 3/1990 | European Pat. Off. . |
| 259044 | 8/1988 | Germany . |
| 63-63859 | 12/1988 | Japan . |
| 2147956 | 6/1990 | Japan . |
| 2190490 | 11/1987 | United Kingdom . |
| WO8100725 | 3/1981 | WIPO . |
| WO8500663 | 2/1985 | WIPO . |
| WO90/05301 | 11/1988 | WIPO . |
| WO9001559 | 2/1990 | WIPO . |

OTHER PUBLICATIONS

Oak Ridge Conference Abstract presented on Apr. 11, 1991.
Loebel, Journal of Clinical Chemistry, 14: 94–102 (1991).
Animal Nutrition 96, Abstract No. 98: 159,456, p. 409 (1993).

*Primary Examiner*—Toni R. Scheiner
*Assistant Examiner*—Susan C. Wolski

[57] ABSTRACT

An assay for photometrically detecting and/or quantitating the presence of an analyte in a sample in which the signal generated by a label associated with the analyte is photometrically detected in the presence of a suspended solid support.

18 Claims, 1 Drawing Sheet

ASSAY WITH SIGNAL DETECTION IN THE PRESENCE OF A SUSPENDED SOLID SUPPORT

This is a continuation of application Ser. No. 07/7736,543 filed Jul. 26, 1991, now abandoned.

FIELD OF THE INVENTION

This invention relates generally to heterogeneous assays and, in particular, to detecting and/or quantitating the presence of analyte in a sample by photometrically detecting a signal generated by a label associated with the analyte in the presence of a suspended solid support.

BACKGROUND OF THE INVENTION

Solid phase assays can be performed in a number of different formats. Many of the currently available systems utilize a noncompetitive or sequential binding format.

For example, in the case of immunoassays, antibody is bound to a solid phase surface either by nonspecific adsorption or by a covalent attachment. The clinical specimen or tissue culture fluid is added to the solid phase and, following sufficient periods of time for reaction, is removed by means of a washing procedure. A second antibody is then added which will react with antigenic sites which are present on the added antigen but which have not been occupied by binding to the solid phase antibody. In some formats, this antibody is directly linked with the label. In such cases, the reaction is completed by washing unbound antibody and measuring the amount of label bound to the solid phase surface.

Alternatively, the second antibody can be added in an unlabeled form and its presence can be quantitated by the addition of another immunoreactant which will bind specifically with the second antibody (an indirect format). The second antibody can also be labeled with a nonenzymatic moiety and the reaction can be quantitated by the addition of reactant which will recognize that moiety specifically, e.g., streptavidin-biotin immunoassay. In all cases unreacted labeled antibody is removed by washing and the amount of label bound to the solid phase is determined by the appropriate instrumentation.

U.S. Pat. No. 4,656,143, issued to Baker et al. on Apr. 7, 1987, describes a heterogenous binding assay in which a liquid component and a granular particulate solid phase are incubated together for a predetermined period of time characterized in that the density of the liquid component is maintained substantially equal to the density of the granular particulate solid phase at least during the predetermined period of time. The density of the liquid component is maintained substantially equal to the density of the granular particulate solid phase by the addition of a density modifying medium having a density greater than the density of the granular particulate solid phase.

U.S. Pat. No. 4,914,023, issued to Philo on Apr. 3, 1990, describes a method of extending the linear range of an enzyme immunoassay by measuring off-peak absorbance.

European Patent Application Publication Number 288,179 published on Oct. 26, 1988 describes a method for detecting the MB isoenzyme of creatine kinase in a biological fluid which comprises (a) forming a mixture of a sample of biological fluid, an immobilized antibody to the B monomer of creatine kinase, and a labeled monoclonal antibody to the MB isoenzyme of creatine kinase; (b) incubating the mixture; (c) separating the solid support from the mixture; and (d) detecting the amount of label associated with the solid support.

U.S. Pat. No. 4,098,876, issued to Piasio et al. on Jul. 4, 1978, describes a reverse sandwich immunoassay which involves incubating a fluid with labeled antibodies to the analyte to be detected to form a labeled antibody-analyte complex and then incubating that complex with immobilized antibodies to the analyte to form a label antibody-analyte-immobilized antibody complex which is separated from the incubation medium.

U.S. Pat. No. 4,244,940, issued to Jeong et al. on Jan. 13, 1981, describes a two-site immunoassay in which sample containing the analyte, a labeled receptor for the analyte, and an unlabeled receptor bound to a solid phase support are incubated together in an aqueous medium to form a substantially stable suspension. The solid and liquid phases are separated and either phase analyzed for the labeled receptor, the concentration of which is a function of the concentration of ligand in the sample.

UK Patent Application Number GB 2 190 490 A published on Nov. 18, 1987 describes an enzyme immunoassay in which an immune complex is obtained by simultaneously reacting the antigen, an immobilized first antibody and a second antibody with an enzyme-labelled third anti-second antibody, separating the solid phase from the liquid phase, and measuring the amount of enzyme activity present in the solid phase.

SUMMARY OF THE INVENTION

This invention concerns an assay to detect and/or quantitate the presence or absence of an analyte in a sample which comprises photometrically detecting and/or quantitating a signal generated by a label associated with the analyte wherein detection is made in the presence of a suspended solid support.

In another embodiment this invention concerns an assay to detect or quantitate the presence of an analyte in a sample in the presence of a suspended solid support which comprises:
  a) reacting a capture reagent immobilized on a solid support with a sample containing the analyte to form an immobilized capture reagent-analyte complex;
  b) incubating the immobilized capture-reagent analyte complex with a detectably-labelled reagent; and
  c) photometrically detecting and/or quantitating the product of step (b) wherein said detection and/or quantitation is made in the presence of the suspended solid support.

In still another embodiment this invention concerns an assay to detect or quantitate the presence of an analyte in a sample in the presence of a suspended solid support which comprises:
  a) simultaneously reacting a capture reagent immobilized on a solid support, a sample containing the analyte and a detectably-labelled reagent; and
  b) photometrically detecting and/or quantitating the product of step (a) wherein said detection and/or quantitation is made in the presence of the suspended solid support.

In still another embodiment this invention concerns an assay to detect or quantitate the presence of an analyte in a sample in the presence of a suspended solid support which comprises:

a) incubating the sample containing the analyte with a detectably-labelled reagent;
b) reacting the product of step (a) with a capture reagent immobilized on a solid support; and
c) photometrically detecting and/or quantitating the product of step (b) wherein said detection and/or quantitation is made in the presence of the suspended solid support.

DETAILED DESCRIPTION OF THE INVENTION

Figure 1:
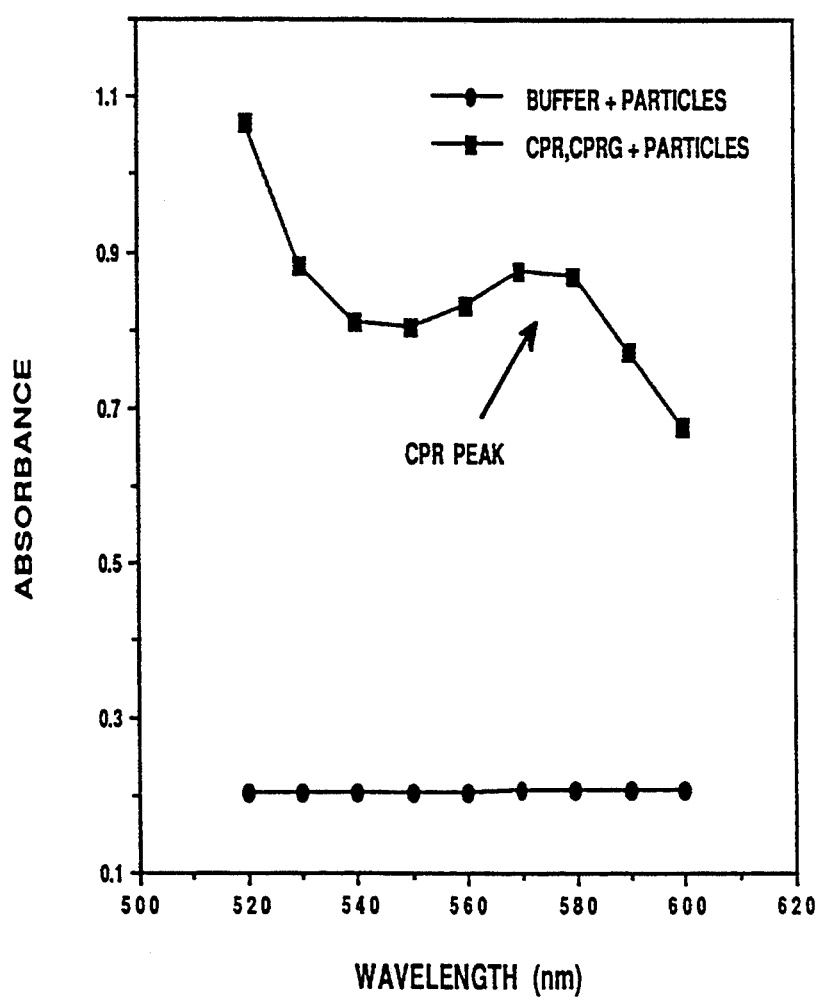
FIGURE 1 depicts the absorption spectrum of chromium dioxide particles in buffer and CPRG and CPR in the presence of chromium dioxide particles.

The term "photometrically detecting and/or quantitating" as used herein means measuring the amount of light absorbed by the solution containing the detectably-labelled reagent using at least two different wavelengths.

The assay of this invention allows one to photometrically detect and/or quantitate the presence or absence of analyte in a sample in the presence of a suspended solid support because photometric detection enables one to correct for the photometric contribution of the solid phase. Depending upon the type of assay performed, the signal generated by the label associated with the analyte can be directly proportional to the amount of analyte present in the sample or inversely proportional to the amount of analyte present in the sample. By "associated with", it is meant that the signal generated by the label can be mathematically correlated either directly or indirectly to the amount of analyte present in the sample. The association between analyte and label does not necessarily have to be a direct physical association.

It is preferred that the assay of this invention be practiced by photometrically detecting at at least two different wavelengths, i.e., at least bichromatically. This approach simplifies the assay process and provides an uncomplicated means of applying assays, such as immunoassays, to automated clinical analyzers like an aca ® discrete clinical analyzer (E. I. du Pont de Nemours and Company, Wilmington, Del.) and Dimension ®.

The assay of this invention is not limited to a particular format nor to a particular analyte. It can be used to perform immunoassays as well as nucleic acid probe assays.

Thus, the assay of this invention concerns an assay to detect and/or quantitate the presence or absence of an analyte in a sample which comprises photometrically detecting and/or quantitating a signal generated by a label associated with the analyte wherein detection is made in the presence of a suspended solid support.

In one embodiment this invention concerns an assay to detect or quantitate the presence of an analyte in a sample in the presence of a suspended solid support which comprises:
a) reacting a capture reagent immobilized on a solid support with a sample containing the analyte to form an immobilized capture reagent-analyte complex;
b) incubating the immobilized capture-reagent analyte complex with a detectably-labelled reagent; and
c) photometrically detecting and/or quantitating the product of step (b) wherein said detection and/or quantitation is made in the presence of the suspended solid support.

In another embodiment this invention concerns an assay to detect or quantitate the presence of an analyte in a sample in the presence of a suspended solid support which comprises:
a) simultaneously reacting a capture reagent immobilized on a solid support, a sample containing the analyte and a detectably-labelled reagent; and
b) photometrically detecting and/or quantitating the product of step (a) wherein said detection and/or quantitation is made in the presence of the suspended solid support.

In still another embodiment this invention concerns an assay to detect or quantitate the presence of an analyte in a sample in the presence of a suspended solid support which comprises:
a) incubating the sample containing the analyte with a detectably-labelled reagent;
b) reacting the product of step (a) with a capture reagent immobilized on a solid support; and
c) photometrically detecting and/or quantitating the product of step (b) wherein said detection and/or quantitation is made in the presence of the suspended solid support.

Suspended solid phases which can be used to practice the invention include coated chromium dioxide particles, iron oxide particles, latex particles, polysaccharide resin-based particles, etc. The preferred solid phase is a coated chromium dioxide particle as described in U.S. Pat. No. 4,661,408, issued to Lau et al. on Apr. 28, 1987, the disclosure of which is hereby incorporated by reference. These chromium dioxide particles are sufficiently hydrolytically stable to be useful as solid supports in heterogeneous immunoassays and bioaffinity separations. The core of the particles is acicular, rutile chromium dioxide having a surface area of 5–100 $m^2/g$, coercivity of 100–750 oersteds, remanent magnetization of 5–45 emu/g and saturation magnetization of 8–85 emu/g. These particles are surface stabilized and further stabilized with a coating of $SiO_2$. The silica coated chromium dioxide is then further coated with a silane to both further stabilize the particle and to provide binding sites for proteins.

The assay of the invention can be used to detect and/or quantitate the presence of any analyte. There can be mentioned glycopeptide hormones such as thyroid stimulating hormone (TSH), human chorionic gonadotropin (hCG), carcinoembryonic antigen (CEA), alpha-fetoprotein (AFP), creatine kinase-MB (CKMB), etc.

The capture reagent can be a member of an immune or non-immune specific binding pair. Immune specific binding pairs are exemplified by antigen/antibody systems or hapten-anti-hapten systems. If an antibody is used, it can be polyclonal, monoclonal, or an immunoreactive fragment thereof and can be produced by customary methods familiar to those skilled in the art.

The terms "immunoreactive antibody fragment" or "immunoreactive fragment" mean fragments which contain the binding region of the antibody. Such fragments may be Fab-type fragments which are defined as fragments devoid of the Fc portion, e.g., Fab, Fab', and F (ab')$_2$ fragments, or may be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic. Such fragments can be prepared using conventional procedures well known to those skilled in the art.

Non-immune binding pairs include systems wherein the two components share a natural affinity for each other but are not antibodies. Exemplary non-immune binding pairs include biotin-streptavidin, folic acid-folate binding protein, complementary probe nucleic acids, etc.

The capture reagent can be immobilized to the surface of the solid support using any conventional means known to those skilled in the art such as adsorption, covalent attachment, etc.

Formation of an immobilized capture reagent-analyte complex is detected and/or quantitated using a detectably-labeled reagent. For example, the detectable label can be an enzyme whose product can be detected photometrically. Examples of such enzymes include $\beta$-galactosidase, alkaline phosphatase, horseradish peroxidase, etc. Other examples can be found in Ishikawa et al., Clin. Chem. Acta, 194: 51–74 (1990), the disclosure of which is hereby incorporated by reference. The detectable label is coupled to a member of an immune or non-immune specific binding pair using conventional techniques well known to those skilled in the art.

In another embodiment, an enzyme amplification cascade to enhance detection and quantitation can be used such as that described in PCT Application Publication Number WO 90/01559, published on Feb. 22, 1990, the disclosure of which is hereby incorporated by reference. The amplification assay for hydrolase enzymes described therein is a highly sensitive flavin adenine dinucleotide-3'-phosphate (FADP)-based enzyme amplification cascade developed for the determination of alkaline phosphatase (ALP). The cascade detects ALP via the dephosphorylation of the substrate FADP to produce the cofactor FAD, which binds stoichiometrically to inactive apo d-amino acid oxidase (D-AAO). The resulting active holo D-AAO oxidizes d-proline to produce hydrogen peroxide, which is quantitated by the HRP-mediated conversion of 3,5-dichloro-2-hydroxy-benzenesulfonic acid (DCHBS) and 4-aminoantipyrine (AAP) to a colored product.

In particular, ALP, the reporter enzyme, dephosphorylates FADP to give FAD, the prosthetic group for D-AAO. Both signal-to-noise ratios and sensitivity are enhanced by the amplification characteristics of the cascade, in which a single molecule of ALP produces multiple molecules of FAD. In turn, these FAD molecules bind to an equivalent number of apo D-AAO molecules to convert them to active holo D-AAO molecules. Each molecule of holo D-AAO then produces multiple molecules of hydrogen peroxide, which convert DCHBS and AAP to a colored product. Thus, the final signal results from a multiplicative, two-stage amplification of the original number of ALP molecules. The scheme can also be readily generalized to incorporate other hydrolase enzymes, apoenzymes and detection enzyme systems, including a "tail-end" substrate cycling system for even greater sensitivity.

It is preferred that detection sensitivity and assay precision be enhanced by correcting for the photometric contribution of the solid phase by recording the signal at at least two different wavelengths, one at or near the peak of absorbance of the product and a second reference wavelength away from the peak of absorbance of the product. The value obtained after subtracting the reference wavelength reading from the peak wavelength reading is proportional to the analyte concentration of the sample, i.e., bichromatic detection.

The following examples are intended to illustrate the invention and are not to be construed in any way as a limitation.

EXAMPLES

All examples discussed below utilized an aca ® discrete clinical analyzer (E. I. du Pont de Nemours and Company, Wilmington, Del. 19898). An example of an aca ® is described in U.S. Pat. No. 4,066,412, the disclosure of which is hereby incorporated by reference.

EXAMPLE 1

CKMB Immunoassay on an aca ® a) Cell lines used in the CKMB immunoassay

The cell lines producing the monoclonal antibodies employed were obtained using the procedure described in U.S. Pat. No. 4,912,033 and in Vaidya et al., Clin. Chem. 32(4): 657–663 (1986), the disclosures of which are hereby incorporated by reference.

Once ascites production was complete, monoclonal antibodies so obtained can be purified using any number of standard techniques such as ammonium sulfate precipitation dialysis, affinity chromatography, ion exchange chromatography, etc. These and other methods for the isolation and purification of monoclonal antibodies are described in general by Goding, Monoclonal Antibodies: Principles and Practice, Academic press, London and New York, 1983 and in U.S. Pat. No. 4,533,496 the disclosures of which are hereby incorporated by reference.

The preferred method for purification and isolation was affinity chromatography on protein A sepharose (Pharmacia Fine Chemicals, Uppsala, Sweden). Protein A is a polypeptide (MW 42,000) isolated from Staphylococcus aureus which binds immunoglobulin without interacting with the antigen binding site.

Anti-CKB monoclonal antibody used as the capture reagent immobilized on chromium dioxide particles as described below was obtained as described above. The clone number was 2581BH 1.1, and the monoclonal antibody was of the IgG$_1$ subclass.

The anti-CKMB monoclonal antibody used to produce the immunoreactive fragment described below was obtained as described above. The clone number was 2580 CC 4.2 and the monoclonal antibody was an IgG$_{2b}$ subclass.

Protein A purified antibody was dialyzed overnight at 4° C. against acetate buffer (100 mM sodium acetate, 150 mM sodium chloride, pH 3.5). The dialyzed antibody was diluted to a concentration of 5 mg/mL using dialysis buffer. The antibody solution was placed in a waterbath at 37° C. for 5 to 10 minutes.

A 10 mg/mL solution of pepsin (Sigma Chemical Co., St. Louis, Mo.) was prepared in acetate buffer. The amount of pepsin required to give a weight ratio of antibody to pepsin of 50:1 was calculated. The antibody solution was stirred while adding the pepsin. The mixture was incubated for 10–15 minutes. The reaction was stopped by slowly adding 3.5 M Tris base dropwise until the pH of the solution was in the range of 7.0 to 8.0. The F(ab')$_2$ preparation was passed through 15–20 mL of protein A—sepharose in a 2.2×25 cm column at a flow rate of 4–4.5 mL per hour. The protein peak was monitored by recording the absorbance of the fractions at 280 nm. The protein peak was collected and concentrated to about 30 mg/mL using an Amicon stirred cell fitted with a 62 mm PM 30 membrane filter. Sterilized F (ab')$_2$ concentrate was filtered and stored at −20° C.

b) Preparation of F (ab')$_2$ β-galactosidase conjugate.

Anti-CKMB antibody fragment as described above was coupled to β-galactosidase using the procedure substantially as described by Kitagawa et al., Enzyme labeling with N-hydroxysuccinimidyl ester of maleimide in "Enzyme Immunoassays, Ishikawa et al., Eds., pp 81–90 (1981), the disclosure of which is hereby incorporated by reference. The conjugate was prepared as follows:

Anti-CKMB monoclonal antibody F (ab')$_2$ fragment was dialyzed against antibody dialysis buffer (20 mM phosphate buffer, 300 mM NaCl, pH 7.0). One mole of F(ab')$_2$ was mixed with 30 moles of SMCC [N-succinimidyl 4-(N-maleimido methyl) cyclohexane-1-carboxylate] and incubated at room temperature for 35 min. with constant stirring. The mixture was loaded on a Sephadex G-25 column (2.2×13 cm) equipped with the UV detector (absorbance 280 nm). Activated F (ab')$_2$ fragment was eluted using antibody dialysis buffer. The protein peak was collected. Volume was recorded and the protein concentration was estimated. One mole of E. coli β-galactosidase [equivalent to SMCC activated F (ab')$_2$] purchased from Boehringer Mannheim was dissolved in antibody dialysis buffer. Activated F(ab')$_2$ was mixed with β-galactosidase and incubated for at least 25 min at 25° C. constantly stirring. Synthesis of the conjugate was monitored using a LKB HPLC equipped with 100 μL loop GF 450 analytical column. The reaction was quenched when the leading peak extended beyond the second peak on the chromatogram by adding 10 μL of 0.1M N-ethylmalemide solution for every mL of conjugate reaction mixture. The mixture was concentrated to 4.0 mL using an Amicon stir cell and YM 100 filter (both from Areicon). Conjugate concentrate was filtered through 0.2 μ syringe filter and purified using LKB HPLC equipped with 1 mL loop GF 450 column, UV monitor, fraction collector and chart recorder. Appropriate fractions were collected and pooled and absorbance was measured at 280 nm wavelength to estimate the protein concentration. The resulting concentrate was filtered, sterilized and stored at 4° C. Conjugate concentrate was diluted as needed in the β-galactosidase conjugate dilution buffer (33.5 g PIPES [piperazine-N,N'-bis [2-ethanesulfonic acid]) 0.2 g MgCl$_2$, 29.2 g NaCl, 100 g bovine serum albumin, and 0.167 g mouse IgG per liter of deionized water, pH 7.0) for the CKMB assay.

c) Anti-CKB Capture Antibody Coupled to Chromium Dioxide Particles

Anti-CKB antibody was immobilized on chromium dioxide particles substantially according to the procedure described by Birkmeyer et al. (Birkmeyer, et al. Application of novel chromium dioxide magnetic particles to immunoassay development. Clin. Chem. 33, 1543–1547, 1987), the disclosure of which is hereby incorporated by reference.

4 liters of coupling buffer was prepared by mixing 196 mls of 10 mM KH$_2$PO$_4$ monobasic and 204 mls of 10 mM K$_2$HPO$_4$ dibasic and increasing the volume to 4 liters using deionized water. pH was adjusted to 7.0. Anti-CKB monoclonal antibody (2581 BH 1.1) was dialyzed overnight against coupling buffer which was changed and dialysis continued for an additional four hours. The volume of the dialyzed antibody was measured, and protein concentration was estimated. The antibody solution was diluted to 2 mg/mL with the coupling buffer. Equal volumes of diluted antibody (2 mg/mL) and 5% suspension of gluteraldehyde activated chromium dioxide particles were mixed together in a tissue culture flask. (Final reaction volume was 200 mL in this experiment). Mixture was allowed to mix overnight at 4° C. The particles were allowed to separate for 60 minutes by placing the tissue culture flask on a magnetic plate at room temperature. The supernatant was removed, and an aliquot was saved for estimating the amount of antibody bound to the particles. More than 98% of the antibody was bound to the particles under these conditions. The reaction was quenched with 200 ml of quench solution (2.0M glycine buffer) and allowed to rock for one hour at room temperature. The particles were separated for 30 minutes on a magnetic plate. The supernatant was removed and then washed 10 times with 150 ml of wash buffer (10 mM potassium phosphate buffer, 0.1% bovine serum albumin, pH 7.4) in a tissue culture flask. Supernatant from the last wash was discarded. 200 ml of storage buffer (10 mM potassium phosphate buffer, 0.1% bovine serum albumin, 0.01% thimerosal, pH 7.4) was added to the particle suspension and stored at 4° C. Ten μL of the particle suspension contained 10 μg of anti-CKB antibody and 250 μg of chromium dioxide.

d) Selection of wavelengths for measuring β-galactosidase activity in an endpoint mode for CKMB The immunoassay for CKMB described herein for an automated immunoassay used β-galactosidase as the reporter enzyme, i.e., the detectable label. β-galactosidase activity was measured using chlorophenol red galactoside (CPRG) as substrate whereby the enzyme reacted with CPRG to produce chlorophenol red (CPR). Approximately, 3 mg of CPRG was used per assay. The maximum absorbance of CPRG was at 412 nm.

CPR, on the other hand, has a maximum absorbance at 577 nm. The amount of CPR formed by the enzyme is less than 1% of the CPRG. FIG. 1 shows the absorption spectrum of chromium dioxide particles in buffer and also CPRG and CPR in the presence of chromium dioxide particles.

It was found that a bichromatic endpoint measurement gave good reproducible measurements. The primary wavelength selected was 577 nm because CPR absorbs maximally at that wavelength. Use of 600 nm wavelength as a blank gave satisfactory performance. It was determined that a 620 nm filter was needed to obtained best results with the detection system. Lower wavelengths such as 510 and 540 nm can also be used but they fall on the descending slope of the CPRG peak and therefore may be sensitive to variation of the CPRG concentration.

Thus, the preferred measurement system should measure the product of the β-galactosidase activity at the primary wavelength of 577 nm and secondary wavelength of 600 nm or above. Subtraction of the reading obtained from the secondary wavelength from the reading obtained from the primary wavelength allowed precise measurement of the enzyme activity.

EXAMPLE 2

CKMB immunoassay a) Reagents
1. CKMB Calibrators: 0, 12.5, 25, 50, 100 and 200 ng of canine CKMB per mL or 0, 13.8, 32, 64 and 128 ng of human CKMB per ml. Purified human or canine CKMB (Aalto Scientific Ltd., Vista, Calif.) was added to CKMB-free human serum pool.

2. Anti-CKB chromium dioxide particles were prepared as described above.
3. Anti-CKMB F (ab')$_2$ $\beta$-galactosidase conjugate concentrate was prepared as described above.
4. Conjugate dilution buffer contained 100 g bovine serum albumin, 33.5 g, sodium PIPES, 29.2 g sodium chloride and 0.2 g magnesium chloride, per liter of deionized water, pH 7.0.
5. Wash buffer consisted of 250 mM Tris, 50 mM sodium borate, pH 7.85.
6. Resuspension buffer consisted of 0.03M HEPES, 0.02M sodium HEPES, 0.01M magnesium acetate, and 0.005% Tween 20, pH 7.6.
7. CPRG tablet containing 3 mg chlorophenol red galactoside, 8.75 mg trehalose, 30 mg mannitol and 3.15 mg carbowax (20 micron) was prepared using the process substantially as disclosed in U.S. Pat. No. 3,932,943 issued to Briggs et al., on Jan. 20, 1976), the disclosure of which is hereby incorporated by reference.
8. HEPES ((n-[2-hydroxyethyl]piperazine-N'-[2-ethanesulfonic acid)) tablet containing 40.4 mg sodium HEPES, 22.8 mg HEPES, 7.0 mg sorbitol, 1.15 mg magnesium acetate, and 4.0 mg carbowax (20 micron) was prepared using the process substantially as disclosed in U.S. Pat. No. 3,932,943 issued to Briggs et al., on Jan. 20, 1976, the disclosure of which is hereby incorporated by reference.

b) Protocol

Ten $\mu$g of anti-CKB antibody coated on chromium dioxide particles as described above was dispensed in a reaction tube along with 300 $\mu$L of appropriately diluted conjugate into the tube. 300 $\mu$L of sample or calibrator was dispensed into the tube which was then vortexed and placed in a waterbath at 37° C. for 15 min and mixed every 2 min. After the incubation period, the particles were separated by placing the tubes in a Corning magnetic test tube stand. Supernatant was aspirated and then 500 $\mu$L of wash buffer was added and the particles were resuspended. This step was repeated 3 times. 75 $\mu$L of resuspension buffer was added after the last wash step and the particles were again resuspended. 60 BL of particle suspension was dispensed into a pack. $\beta$-galactosidase activity bound to the particles was measured on the aca ® (E. I. du Pont de Nemours and Company, Wilmington, Del. 19898). aca ® CPRG packs (standard aca ® discrete clinical analyzer packs available from E. I. du Pont de Nemours and Company, Wilmington, Del.) for use with the aca ® discrete clinical analyzer, containing a HEPES tablet in dimple 2, and a CPRG tablet in dimple 3, where dimples 2 and 3 refer to tablet storage areas in a standard aca ® discrete clinical analyzer pack, a CPRG tablet contains 3 mg chlorophenol red galactoside, 8.75 mg trehalose, 30 mg mannitol and 3.15 mg carbowax [20 micron] prepared using the process substantially as disclosed in U.S. Pat. No. 3,932,943 issued to Briggs et al., on Jan. 20, 1976), the disclosure of which is hereby incorporated by reference, and a HEPES tablet contains (40.4 mg sodium HEPES, 22.8 mg HEPES, 7.0 mg sorbitol, 1.15 mg magnesium acetate, and 4.0 mg carbowax [20 micron] prepared using standard tableting processes known in the art).

The packs were then sealed with cellophane tape and the $\beta$-galactosidase activity bound to the particles was measured using the aca ® discrete clinical analyzer as follows. Once the pack was loaded on the aca ®, 2 mL of phosphate buffer, pH 7.8, and 3 mL of water were dispensed into the pack. Breaker mixer 1 (a component of the aca ® discrete clinical analyzer which breaks tablet reagents and facilitates the mixing reagents) was utilized to dissolve the HEPES and CPRG tablets and suspend the particles. Bound enzyme reacted with CPRG to form CPR at 37° C. After 4.2 min the CPR formed was measured at 577 and 600 nm wavelengths. 577 was the primary wavelength at which the CPR has maximum absorbance, and 600 nm was the blanking wavelength. The 600 nm reading was subtracted from the 577 reading to eliminate interference due to suspended particles. The 577 minus 600 nm reading, called the endpoint reading in aca ®, was plotted against the bottle values of the CKMB calibrators to generate a standard curve.

c) Results

CKMB standard curves were generated using canine CKMB (Table 1) and human CKMB (Table 2) calibrators. The assay was performed as described above. The final absorbance was read using the aca ® at wavelengths of 577 and 600 nm. Results are presented in Tables 1 and 2.

TABLE 1

DATA FOR CKMB STANDARD CURVE USING CANINE CKMB

| CANINE CKMB (ng/mL) | REPLICATES | ENDPOINT READING (577–600 nm) mA | STANDARD DEVIATION | COEFFICIENT OF VARIATION |
| --- | --- | --- | --- | --- |
| 0 | 5 | 116.8 | 1.5 | 1.3 |
| 12.5 | 5 | 140.4 | 2.6 | 1.8 |
| 25 | 5 | 171.9 | 6.2 | 3.6 |
| 50 | 5 | 207.8 | 6.6 | 3.2 |
| 100 | 5 | 317.2 | 8.5 | 2.9 |
| 200 | 5 | 510.6 | 13.6 | 2.7 |

TABLE 2

DATA FOR CKMB STANDARD CURVE USING HUMAN CKMB

| HUMAN CKMB (ng/mL) | REPLICATES | ENDPOINT READING (577–600 nm) mA | STANDARD DEVIATION | COEFFICIENT OF VARIATION |
| --- | --- | --- | --- | --- |
| 0 | 3 | 92.2 | 0.4 | 0.5 |
| 13.8 | 3 | 119.5 | 2.1 | 1.8 |

TABLE 2-continued

DATA FOR CKMB STANDARD CURVE USING HUMAN CKMB

| HUMAN CKMB (ng/mL) | REPLICATES | ENDPOINT READING (577–600 nm) mA | STANDARD DEVIATION | COEFFICIENT OF VARIATION |
|---|---|---|---|---|
| 32 | 3 | 165.1 | 1.7 | 1.0 |
| 64 | 3 | 250.9 | 5.4 | 2.2 |
| 128 | 3 | 427.43 | 6.5 | 1.5 |

EXAMPLE 3

Within Run Precision

The within run precision and analytical sensitivity of the CKMB assay were established by analyzing three levels of control material. The sensitivity of the CKMB assay was defined as two standard deviations of the zero level control material. Results are presented in Table 3.

TABLE 3

WITHIN RUN PRECISION AND SENSITIVITY OF CKMB ASSAY

| REPLICATES | MEAN CKMB (ng/mL) | STANDARD DEVIATION | COEFFICIENT OF VARIATION |
|---|---|---|---|
| 10 SENSITIVITY | −0.15 (2SD OF ZERO) | 0.12 0.24 | 77.2 |
| 10 | 4.8 | 0.3 | 6.3 |
| 10 | 77.3 | 2.9 | 3.8 |

EXAMPLE 4 hCG Immunoassay a) Preparation of F(ab')$_2$ $\beta$-galactosidase conjugate reagent Anti-hCG monoclonal antibody (Hybritech 514) used in preparing the detector antibody fragment conjugate was purchased from Hybritech Inc., P.O. Box 269006, San Diego, Calif. 92126. This antibody was a beta chain specific monoclonal antibody having an affinity of approximately $3 \times 10^{-10}$ M. However, any anti-hCG monoclonal antibody having sufficient affinity for use in an immunoassay format can be used, and such antibodies can be prepared using techniques well known to those skilled in the art, e.g., Kohler and Milstein, Nature, 256: 495–497 (Aug. 7, 1975). The F(ab')$_2$ fragment and F(ab')$_2$ $\beta$-galactosidase conjugate were prepared as described above in Example 1.

A solution of concentrated conjugate prepared as described above in Example 1 was diluted with a volume of the $\beta$-galactosidase conjugate dilution buffer (containing 100 mM PIPES, 1 mM MgCl$_2$, 500 mM NaCl, 10%(w/v) bovine serum albumin, and 167 µg/ml protein-A purified mouse IgG, pH 7.0) to a final concentration of $4 \times 10^{-9}$ M $\beta$-galactosidase.

b) Anti-hCG Capture Antibody Coupled to Chromium Dioxide Particles

Chromium dioxide particles were prepared substantially as described in U.S. Pat. No. 4,661,408 issued to Lau et al.. on Apr. 28, 1987, the disclosure of which is hereby incorporated by reference. Anti-hCG antibody (Du Pont cell line 34/25) used as the capture antibody was prepared using whole molecule hCG as immunogen and conventional techniques known in the art for the production of monoclonal antibodies. See, Kohler and Milstein article mentioned above. The antibody used was an alpha-chain specific anti-hCG monoclonal antibody having an affinity of approximately $3 \times 10^{-10}$ M. However, any anti-hCG monoclonal antibody having sufficient affinity for use in an immunoassay format can be used, and such antibodies can be prepared using techniques known in the art for the production of monoclonal antibodies. Again, the immunoassay of this invention can be practiced using any antibody and/or immunoreactive fragment suitable for use in an immunoassay.

Capture anti-hCG antibody was coupled to chromium dioxide particles as described above in Example 1. A concentration of 0.75 mg anti-HCG capture antibody/mL chromium dioxide particles was added to a slurry of chromium dioxide particles containing 25 mg/mL solids. The anti-HCG capture antibody coated chromium dioxide particle slurry thus obtained was made into tablets containing 3.0 mg antibody-coated chromium dioxide particles per tablet, with 9.83 mg trehalose, 0.98 mg carbowax, and 0.03 mg thimerosol added as inert materials. The tablets were prepared using the process substantially as disclosed in U.S. Pat. No. 3,932,943 issued to Briggs et al., on Jan. 20, 1976, the disclosure of which is hereby incorporated by reference.

c) Effect of Presence of Suspended Chromium Dioxide Particles In aca® Discrete Clinical Analyzer Pack On Chlorophenol Red Galactoside (CPRG) Absorbance The effect of chromium dioxide particles on the absorbance of CPRG in aca® discrete clinical analyzer packs was measured. Three sets of ten tubes each were prepared with each set (designated as i, ii, and iii below) containing:

i) Resuspension Buffer consisted of 0.03M HEPES, 0.02M sodium HEPES 0.01M magnesium acetate, and 0.005% Tween 20, pH 7.6.

ii) Resuspension Buffer and Anti-hCG capture antibody coated chromium dioxide particles: 5 chrome tablets having 3 mg chrome solids each were dissolved in 3 ml water to produce a solution having 5 mg/ml solids. 75 µl containing 250 µg chrome solids was added to each tube.

iii) Resuspension Buffer and Anti-hCG capture antibody coated chromium dioxide particles treated with hCG 0 calibrator (horse serum obtained from Pel-Freez Biologicals, Rogers, Ariz. 72756).

As indicated above, 75 µl of anti-HCG capture antibody coated chromium dioxide particles was dispensed into each of 20, 12 mm×75 mm polyethylene tubes (sets ii and iii). 400 µl of appropriately diluted F(ab')$_2$ $\beta$-galactosidase conjugate reagent ($\beta$-galactosidase-tag antibody conjugate diluted with conjugate dilution buffer containing 100 mM PIPES, 1 mM MgCl$_2$, 500 mM NaCl, 10%(w/v) bovine serum albumin, and 167 µg/ml protein-A purified mouse IgG, pH 7.0) was added into each of 10 tubes (set iii). 100 µL of hCG 0 calibrator was added to each tube in set iii. The contents of each of the tubes was mixed by vortexing and placed in a 37° C. heating block for 15 minutes. After 15 minutes, the particles were separated by placing the tubes in a magnetic test tube stand such that the particles were held magnetically against the sides of the test tube. The supernatant of each tube was removed by aspiration, 500 μL of wash buffer (250 mM Tris, 50 mM sodium borate, pH 7.85) was added to each tube and the particles were resuspended by vortexing. The wash procedure was repeated two additional times. After the last wash, 75 μL of resuspension buffer (0.03M HEPES, 0.02M sodium HEPES, 0.01M magnesium acetate, and 0.005% Tween 20, pH 7.6) was added, the particles were resuspended by vortexing.

60 μL from all tubes in sets i, ii, and iii were dispensed into dimple 1 of aca ® CPRG packs standard aca ® discrete clinical analyzer packs (available from E. I. du Pont de Nemours and Company, Wilmington, DE for use with the aca ® discrete clinical analyzer), containing a HEPES tablet in dimple 2, and a CPRG tablet in dimple 3, where dimples 2 and 3 refer to tablet storage areas in a standard aca ® discrete clinical analyzer pack, a CPRG tablet contains 3 mg chlorophenol red galactoside, 8.75 mg trehalose, 30 mg mannitol and 3.15 mg carbowax [20 micron] (prepared using the process substantially as disclosed in U.S. Pat. No. 3,932,943 issued to Briggs et al., on Jan. 20, 1976), the disclosure of which is hereby incorporated by reference, and a HEPES tablet contains 40.4 mg sodium HEPES, 22.8 mg HEPES, 7.0 mg sorbitol, 1.15 mg magnesium acetate, and 4.0 mg carbowax [20 micron] prepared using standard tableting processes known in the art. The packs were then sealed with cellophane tape and the β-galactosidase activity bound to the particles was measured using the aca ® discrete clinical analyzer as follows. Once the pack was loaded on the aca ®, 2 mL of phosphate buffer, pH 7.8, and 3 mL of water was dispensed into the pack. Breaker mixer 1 (a component of the aca ® discrete clinical analyzer which breaks tablet reagents and facilitates the mixing reagents) was utilized to dissolve the HEPES and CPRG tablets and suspend the particles. Bound β-galactosidase enzyme reacted with CPRG to form chlorophenol red (CPR) at 37° C. After 4.2 minutes the CPR formed was measured at 577 and 600 nm wavelengths. 577 is the primary wavelength at which the CPR has maximum absorbance, and 00 nm is the blanking wavelength. The 600 nm reading was subtracted from the 577 reading. The results are shown in Table 1.

TABLE 1

Effect of Presence of Suspended Chromium Dioxide Particles in aca ® Discrete Clinical Analyzer Pack On Chlorophenol Red Galactoside (CPRG) Absorbance

| $CrO_2$ *(+/−) | hCG Calibrator | Bichromatic Endpoint Reading (577−600 nm) mA | SD | Coefficient Of Variation |
|---|---|---|---|---|
| − | None | 51.4 | 0.44 | 0.86 |
| + | None | 50.5 | 0.51 | 1.0 |
| + | 0 | 51.8 | 0.51 | 0.98 |

*+ indicates presence of chromium dioxide particles
− indicates absence of chromium dioxide particles The results in Table 1 indicate no significant difference between the bichromatic endpoint readings (measurement of absorbance at 577 nm minus measurement at 600 nm) obtained in the presence and absence of suspended chromium dioxide particles.

EXAMPLE 5 hCG Standard Curve Generated With Chromium Dioxide Particles Present in aca ® Discrete Clinical Analyzer Pack The precision, accuracy, curve shape, and range of the immunoassay format of the present invention as applied to the analyte hCG were evaluated as described below.

75 μl chromium dioxide particle solution containing 250 μg chromium solids and anti-HCG capture antibody were dispensed into each of 15, 12 mm×75 mm polyethylene tubes. 400 μl of appropriately diluted β-galactosidase-tag antibody conjugate ($4 \times 10^{-9}$M β-galactosidase-tag antibody conjugate diluted with conjugate dilution buffer containing 100 mM PIPES, 1 mM $MgCl_2$, 500 mM NaCl, 10%(w/v) bovine serum albumin, and 167 μg/ml protein-A purified mouse IgG, pH 7.0) was added into each of 10 tubes. 100 μL of each of a series of hCG calibrators (0, 25, 100, 300 and 500 mIU/mL of human hCG per mL; hCG was purified from the urine of pregnant women and standardized according to the 1st International Reference Preparation [First IRP] from the World Health Organization) was added to a series of tubes (duplicate tubes were prepared for each calibrator concentration); the contents of which were then mixed by vortexing and placed in a 37° C. heating block for 15 minutes. After 15 minutes, the particles were separated by placing the tubes in a magnetic test tube stand such that the particles were held magnetically against the sides and bottom of the test tube. The supernatant of each tube was removed by aspiration, 500 μL of wash buffer (250 mM Tris, 50 mM sodium borate, pH 7.85) was added to each tube and the particles were resuspended by vortexing. The wash procedure was repeated two additional times. After the last wash, 75 μL of resuspension buffer (0.03M HEPES, 0.02 sodium HEPES, 0.01M magnesium acetate, and 0.005% Tween 20, pH 7.6) was added, the particles were resuspended by vortexing.

60 μL from each tube were dispensed into dimple 1 of aca ® CPRG packs (standard aca ® discrete clinical analyzer packs available from E. I. du Pont de Nemours and Company, Wilmington, Del. for use with an aca ® discrete clinical analyzer, containing a HEPES tablet in dimple 2, and a CPRG tablet in dimple 3, where dimples 2 and 3 refer to tablet storage areas in a standard aca ® discrete clinical analyzer pack, a CPRG tablet contains 3 mg chlorophenol red galactoside, 8.75 mg trehalose, 30 mg mannitol and 3.15 mg carbowax [20 micron] prepared using the process substantially as disclosed in U.S. Pat. No. 3,932,943 issued to Briggs et al., on Jan. 20, 1976, and a HEPES tablet contains 40.4 mg sodium HEPES, 22.8 mg HEPES, 7.0 mg sorbitol, 1.15 mg magnesium acetate, and 4.0 mg carbowax [20 micron] prepared using standard tableting processes known in the art. The packs were sealed with cellophane tape and the activity of β-galactosidase bound to the particles measured on the aca ®. Measurements are obtained on the aca ® as described above in Example 4. The measurement at 577 nm minus the measurement at 600 nm, called the bichromatic reading on the aca ®, was plotted against the concentration of the hCG calibrators to generate a standard curve. The results are presented in Table 2.

TABLE 2 hCG immunoassay Standard Curve

| hCG mIU/ml | Replicates | Bichromatic Endpoint (577–600 nm) mA | SD | Monochromatic Endpoint (577 nm) mA | SD |
|---|---|---|---|---|---|
| 0 | 3 | −23.0 | 0.87 | 318.8 | 6.5 |
| 25 | 3 | −4.45 | 1.1 | 352.8 | 10 |
| 100 | 3 | 80.8 | 2.0 | 532.5 | 4.1 |
| 300 | 3 | 283.5 | 8.8 | 944.0 | 19.3 |
| 500 | 3 | 440.8 | 37.7 | 1274 | 83.8 |

The results presented in Table 2 demonstrate that a standard curve can be generated in an immunoassay for hCG over a range of 0–500 mIU/ml in the presence of suspended chromium dioxide particles, and further that the precision of a bichromatic reading (measurement at 77 nm minus measurement at 699 nm) was significantly better than that obtained with a monochromatic reading.

EXAMPLE 6

The precision, sensitivity, standard curve, and range of the immunoassay format of the present invention as applied to the analyte TSH were evaluated as described below.

a) Preparation of TSH conjugate concentrate: Preparation of Anti-TSH-F(ab')$_2$-Alkaline Phosphatase Conjugate i) Functionalization of anti-TSH-F (ab')$_2$ with a Thiol Reactive Group Anti-TSH-F (ab')$_2$ antibody fragments were prepared from an anti-TSH monoclonal IgG antibody obtained from the Hybritech hybridoma cell line identified as 972.2. IgG was isolated from ascites fluid derived from the cell line by affinity chromatography using a Protein-A-sepharose CL 4B column (Pharmacia Co.). IgG was eluted from the column with sodium acetate buffer, pH 3.0 and then dialyzed against 10 mM sodium phosphate and 300 mM sodium chloride solution, pH 7.0. The isolated IgG solution was then digested with a 50:1 molar ratio of pepsin at 37° C. for 65 minutes. Anti-TSH-F(ab')$_2$ antibody fragments were isolated from the resulting solution by affinity chromatography using a protein-A-sepharose CL 4B column (Pharmacia Co.). The anti-TSHF(ab')$_2$ antibody fragments were eluted from the column with 1M glycine, 1M sodium chloride, pH 8.6, and then purified by HPLC size exclusion column chromatography using a GF-250 XL column (Du Pont Co.). 1 mL of a solution containing 5 mg/mL anti-TSH-F(ab')$_2$ was dialyzed against 1000 volumes of 10 mM Na-phosphate/300 mM NaCl buffer, pH 7.0, and held overnight at 2°–8° C. with constant stirring. After dialysis, the F (ab')$_2$ containing solution was transferred into a dark vial. The antibody fragment solution was then treated with a 10 fold molar excess of the cross-linking reagent, N-succinimidyl -4- (N-maleimidomethyl) cyclo-hexane-1-carboxylate (SMCC) (Pierce Co.) in dimethyl sulfoxide (DMSO). The reaction mixture was allowed to rock gently at room temperature for 30 minutes. The mixture was then loaded onto a Sephadex G-25 column (1.0 cm×30 cm), and eluted with 10 mM Na-phosphate/300 mM NaCl buffer, pH 6.5. The fractions were collected and pooled to provide the maleimide-functionalized F (ab')$_2$ solution.

ii) Functionalization of alkaline phosphatase 1 mL of a 10 mg/mL solution of alkaline phosphatase stock solution (Boehringer-Mannheim Biochemicals) was dialyzed against 1000 volumes of 10 mM Na-phosphate/300 mM NaCl buffer, pH 7.0, and held overnight at 2°–8° C. with constant stirring. After dialysis, the enzyme solution was transferred to a dark vial and the protein concentration adjusted by adding dialysis buffer to the solution. The final enzyme solution protein concentration was adjusted to 5 mg/mL. The enzyme solution was treated with a 15 fold molar excess of N-succinimidyl-S-acetylthioacetate (SATA) (Calbiochem.) in dimethyl sulfoxide (DMSO) to introduce blocked thiol groups. The reaction mixture was allowed to rock gently at room temperature for 30 minutes, loaded onto a Sephadex G-25 column (1.0×30 cm), and then eluted with 10 mM Na-phosphate/300 mM NaCl buffer, pH 6.5. The fractions were collected and pooled to provide acetylthiolated alkaline phosphatase.

iii) Deblocking and Conjugation 2.9 mL of a 1.10 mg/mL solution of maleimide-functionalized anti-TSH-F (ab')$_2$ was added to 4.1 mL of a 1 mg/mL solution of acetylthiolated alkaline phosphatase (AP) and treated with 210 µL of 1M hydroxylamine, pH 7.0. The reaction mixture was allowed to rock gently at room temperature for 60 minutes. The conjugation reaction was monitored by HPLC using a GF-450 size exclusion column (9.4 cm×25 cm) (Du Pont Co.) until the reaction was complete.

Conjugation reaction was quenched at room temperature by the addition of 7 µL of 0.1M N-ethylmaleimide (NEM) solution. After 30 minutes the crude conjugate solution was concentrated (using an Amicon stirred-cell, PM 30 membrane) to 2 mL.

iv) Conjugate Separation

The anti-TSH-F (ab')$_2$-alkaline phosphatase conjugate was purified by HPLC using a GF-450 XL size exclusion column (22.5 mm×25 cm). The conjugate was eluted with 0.2M Na-phosphate buffer, pH 7.0 at a flow rate of 2 mL/min. The effluent was monitored at 280 nm. Two 1 mL injections were made and the fractions (1.0 ml each) were collected. Fractions having both immunoreactivity and enzymatic activity were pooled.

Conjugate concentrate was diluted to 0.1 absorbance at 280 nm.

b) Antibody-coated chromium dioxide particles

Chromium dioxide magnetic particles containing mouse monoclonal antibody specific to TSH were made. This monoclonal antibody was obtained from Du Pont hybridoma cell line 4/46.2 which was generated by immunizing BALB/c mice with pure whole TSH according to the process described by Freund, *J. Adv. Tuberc. Res.*, F:130–148 (1956). Spleen lymphocytes were obtained and fused with myeloma cells using standard techniques. Galfre et al., *Nature*, 266: 550–552 (1976) . The procedure of Engvall et al., *J. Immunol.*, 109: 129–135 (1972) was used to screen the resulting clones.

c) Preparation of conjugate diluent

Conjugate diluent was prepared as described below:

|  | Diluent concentration |
|---|---|
| TRIS | 1.515 Grams/Liter |
| SODIUM CHLORIDE | 29.23 Grams/Liter |
| MAGNESIUM CHLORIDE | 0.2035 Grams/Liter |
| ZINC CHLORIDE | 0.0135 Grams/Liter |
| BSA 30% SOLUTION | 41.65 mL/Liter |
| MANNITOL 500 MICR | 25 Grams/Liter |

-continued

| | Diluent concentration |
|---|---|
| HORSE SERUM HEAT TREATED | 750 mL/Liter |
| TWEEN 20 | 0.075 mL/Liter |
| AMPHOTERICIN B | 0.01 Grams/Liter |
| 2-CHLOROACETAMIDE | 2.5 Grams/Liter |
| GENTAMYCIN SULFATE | 0.1 Grams/Liter |
| NEOMYCIN SULFATE | 1 Grams/Liter |
| STREPTOMYCIN SULFATE | 0.1 Grams/Liter |

Sample (0.3 mL) (TSH calibrator; level 0, 0.5, 5, 30, 50 BIU/mL), conjugate reagent (0.4 mL) (1/50 dilution of conjugate concentrate in conjugate diluent) and antibody coated chrome (0.05 mL, 125 Bgrams chrome) were incubated at 37° C. for 15 minutes in polypropylene test tubes with periodic vortexing. Particles were magnetically separated and washed 3 times with 1.0 mL aliquots of wash buffer (0.25M Tris HCl, pH 7.85 and 50 mM sodium borate). Following the third wash, particles were resuspended in 0.06 mL 100 mM Tris buffer pH=8.8 and tubes from identical levels pooled. 50 μL of chrome was then placed in dimple 4 of an aca pack. The structure of the chrome is: chrome particles:antibody.TSH:F(ab')$_2$:alkaline phosphatase.

All reagents for the FADP based cascade were included in the pack as follows::FADP was in dimple 2 (breaker mixer 1), apo d-amino acid oxidase was in dimple 6 (breaker mixer 2), HRP, DCHBS, 4-AAP solution were in dimple 5 (breaker mixer 2) and proline was in dimple 1

| Component | Final pack conc | Units | Source |
|---|---|---|---|
| FADP | 3.6 | μg/mL | LBL* |
| MgSO$_4$ | 0.03 | mM | Fischer |
| ZnSO$_4$ | 0.0003 | mM | Sigma |
| d-proline | 24.6 | mM | Sigma |
| apo d-amino acid oxidase | 0.188 | units/mL | LBL* |
| horseradish peroxidase | 0.025 | mg/mL | Shinko |
| 4-AAP | 0.25 | mM | Sigma |
| DCHBS | 2.5 | mM | Sigma |
| Tris HCl pH 8.8 | 100 | mM | Sigma |

*LBL = London Biotechnology, Ltd

Packs were processed on aca. All reactions took place at 37° C. in a 5 ml reaction volume. In the kinetic mode, a 17-second bichromatic (BC) rate measurement was made at 510 and 600 nm. The data were analyzed in both the bichromatic endpoint and bichromatic rate modes. (mA or mA/min) Response was converted to analyte using a Logit equation. The results are summarized below:

Precision ANALYTE RESULTS

| TSH Level μIU/mL | Replicates | BC Endpt Mean A[1] | BC Endpt SD A | BC Rate Mean mA/min | BC Rate SD mA/min |
|---|---|---|---|---|---|
| 0 | 20 | 0.00 | 0.029 | 0.02 | 0.016 |
| 0.5 | 4 | 0.40 | 0.04 | 0.39 | 0.04 |
| 5 | 10 | 5.00 | 0.62 | 5.00 | 0.45 |
| 30 | 10 | 30.06 | 2.33 | 30.16 | 3.19 |
| 50 | 9 | 48.62 | 5.29 | 49.32 | 7.95 |
| Sensitivity | | | 0.06 | | 0.03 |

(Based on 2SDs at 0 TSH)

Standard curve

RESPONSE RESULTS

| TSH Level μIU/mL | Replicates | BC Endpt Mean A | BC Endpt SD A | BC Rate Mean mA/min | BC Rate SD mA/min |
|---|---|---|---|---|---|
| 0 | 20 | 0.027 | 0.0010 | 5.18 | 0.86 |
| 0.5 | 4 | 0.045 | 0.0092 | 25.09 | 2.15 |
| 5 | 10 | 0.184 | 0.0175 | 249.21 | 20.09 |
| 30 | 10 | 0.672 | 0.0320 | 958.66 | 57.09 |
| 50 | 9 | 0.892 | 0.0665 | 1219.78 | 90.45 |

[1]A = absorbance

EXAMPLE 7

This experiment was designed to show the improved variance by using bichromatics vs. monochromatics with chrome in pack. No immunochemistry was used in this experiment. Packs were empty.

TSH chrome was formulated to 125 μ grams chrome per 0.5 ml. 0.5 ml was added per pack on the aca ® and 4.5 mL of 90 mM Tris (pH 8.8) was added to pack as diluent. Pack was processed through aca and measured in photometer at 2 wawelengths as follows:

| Read | Time (seconds) | Wavelength (nm) | Mean (A) | SD (A) |
|---|---|---|---|---|
| A1 | 0 | 510 | 0.24 | 0.03 |
| A2 | 5.3 | 600 | 0.26 | 0.03 |
| A3 | 17.1 | 510 | 0.23 | 0.03 |
| A4 | 22.4 | 600 | 0.25 | 0.03 |
| A2-A1 | | | 0.02 | 0.0007 |
| | | | 0.02 | 0.0007 |
| | | | Mean (A/17 sec) | SD (A/17 sec) |
| (A4-A3)-(A2-A1) | | | 0.001 | 0.0003 |
| A3-A1 | | | -0.003 | 0.0005 |

The bichromatic endpoint measurement (A2-A1) is significantly more precise than the monochromatic endpoint measurements at either the A1 or A2 wavelengths at times 0 and 5.3 seconds. The bichromatic endpoint measurement (A4-A3) is significantly more precise than the monochromatic endpoint measurements at either the A4 or A3 wavelengths at times 17.1 and 22.4 sec. The bichromatic rate measurement ((A4-A3)-(A2-A1)) is more precise than the monochromatic rate measurement (A3-A1).

What is claimed is:

1. An assay to detect or quantitate the presence of an analyte in a sample in the presence of a suspended solid support which comprises:
   a) reacting a capture reagent immobilized on the suspended solid support with a sample containing the analyte wherein said capture reagent specifically binds analyte to form an immobilized capture reagent—analyte complex;
   b) separating any unreacted sample from the immobilized capture reagent—analyte complex;
   c) incubating the immobilized capture reagent—analyte complex with a detectably labelled reagent wherein said detectably labelled reagent specifically binds analyte to form an immobilized capture reagent—analyte—detectably labelled reagent complex and further wherein the detectable label is either (i) photometrically detectable itself or is (ii) an enzyme which produces a photometrically detectable product in the presence of a substrate specific for the enzyme;
d) separating any unbound detectably labelled reagent from the immobilized capture reagent—analyte—detectably labelled reagent complex;
e) measuring the amount of light absorbed by (i) the immobilized capture reagent—analyte—detectably labelled reagent complex when the detectable label is itself photometrically, detectable or (ii) the photometrically detectable product produced upon the addition of substrate when the detectable label is an enzyme, wherein said measurement is made using at least two different wavelengths, a first reference wavelength reading at or near the peak absorbance of the label or product and a second reference wavelength reading away from the peak of absorbance of the label or product and further wherein said measurement is made in the presence of the suspended solid support; and
f) correlating the measurements obtained in step (e) to the quantity and/or presence of analyte, the value obtained after substracting the second reference wavelength reading from the first reference wavelength reading being proportional to the concentration of the analyte in the sample.

2. An assay according to claim 1 wherein the suspended solid support is selected from the group consisting of coated chromium dioxide particles, and iron oxide particles.

3. An assay according to claim 1 wherein the analyte is a glycopeptide hormone.

4. An assay according to claim 1 wherein the analyte selected from the group consisting of TSH, CKMB, and HCG.

5. An assay according to claim 1 wherein detection and/or quantitation is made using an enzyme amplification cascade.

6. An assay according to claim 5 wherein the cascade is an FADP-based enzyme amplification cascade.

7. An assay to detect or quantitate the presence of an analyte in a sample in the presence of a suspended solid support which comprises:
a) simultaneously reacting a capture reagent immobilized on the suspended solid support with a sample containing the analyte and a detectably labelled reagent wherein said capture reagent and said detectably labelled reagent both specifically bind analyte to form a capture reagent—analyte detectably labelled reagent complex wherein the detectable label is either photometrically detectable itself or is (ii) an enzyme which in the presence of a substrate specific for the enzyme produces a photometrically detectable product;
b) separating any unreacted sample and/or any unreacted detectably labelled reagent from the immobilized capture reagent—analyte—detectably labelled reagent complex;
c) measuring the amount of light absorbed by (i) the immobilized capture reagent—analyte—detectably labelled reagent complex when the detectable label is itself photometrically detectable or (ii) the photometrically detectable product produced upon the addition of substrate the detectable label is an enzyme wherein said measurement is made using at least two different wavelengths, a first reference wavelength reading at or near the peak absorbance of the label or product and a second reference wavelength reading away from the peak of absorbance of the label or product, and further wherein said measurement is made in the presence of the suspended solid support; and
d) correlating the measurements obtained in step (c) to the quantity and/or presence of analyte, the value obtained after substracting the second reference wavelength reading from the first reference wavelength reading being proportional to the concentration of the analyte in the sample.

8. An assay according to claim 7 wherein the suspended solid support is selected from the group consisting of coated chromium dioxide particles, and iron oxide particles.

9. An assay according to claim 7 wherein the analyte is a glycopeptide hormone.

10. An assay according to claim 7 wherein the analyte selected from the group consisting of TSH, CKMB, and HCG.

11. An assay according to claim 7 wherein detection and/or quantitation is made using an enzyme amplification cascade.

12. An assay according to claim 11 wherein the cascade is an FADP-based enzyme amplification cascade.

13. An assay to detect or quantitate the presence of an analyte in a sample in the presence of a suspended solid support which comprises:
a) incubating the sample containing the analyte with a detectably labelled reagent which specifically binds analyte to form an analyte—detectably labelled reagent complex wherein the detectable label is either (i) photometrically detectable itself or is (ii) an enzyme which in the presence of a specific for the enzyme produces a photometrically detectable product;
b) reacting the analyte—detectably labelled reagent complex with a capture reagent immobilized on the suspended solid support wherein said capture reagent specifically binds analyte;
c) separating any unbound sample and/or detectably labelled reagent from the immobilized capture reagent—analyte—detectably labelled reagent complex;
d) measuring the amount of light absorbed by (i) the immobilized capture reagent—analyte—detectably labelled reagent complex when the detectable label is itself photometrically detectable or (ii) the photometrically detectable product produced upon the addition of substrate when the detectable label is an enzyme wherein said measurement is made using at least two different wavelengths, a first reference wavelength reading at or near the peak absorbance of the label or product and a second reference wavelength reading away from the peak of absorbance of the label or product, and further wherein said measurement is made in the presence of the suspended solid support; and
e) correlating the measurements obtained in step (d) to the quantity and/or presence of analyte, the value obtained after substracting the second reference wavelength reading from the first reference wavelength reading being proportional to the concentration of the analyte in the sample.

14. An assay according to claim 13 wherein the suspended solid support is selected from the group consisting of coated chromium dioxide particles, and iron oxide particles.

15. An assay according to claim 13 wherein the analyte is a glycopeptide hormone.

16. An assay according to claim 13 wherein the analyte selected from the group consisting of TSH, CKMB, and HCG.

17. An assay according to claim 13 wherein detection and/or quantitation is made using an enzyme amplification cascade.

18. An assay according to claim 17 wherein the cascade is an FADP-based enzyme amplification cascade.

* * * * *